(12) United States Patent
Wark et al.

(10) Patent No.: US 8,630,711 B1
(45) Date of Patent: Jan. 14, 2014

(54) SYSTEMS AND METHODS FOR TREATING DISORDERS BY SELECTIVELY ACTIVATING AND/OR BLOCKING MUSCLES THROUGH INTRAFASICULAR STIMULATION OF THE PUDENDAL NERVE

(75) Inventors: Heather A. C. Wark, Salt Lake City, UT (US); Patrick C. Cartwright, Salt Lake City, UT (US); Richard A. Normann, Park City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 581 days.

(21) Appl. No.: 12/572,866

(22) Filed: Oct. 2, 2009

Related U.S. Application Data (60) Provisional application No. 61/102,255, filed on Oct. 2, 2008.

(51) Int. Cl.
*A61N 1/18* (2006.01)

(52) U.S. Cl.
USPC ............... 607/40; 607/39; 607/41; 607/118; 607/133; 607/138; 607/143; 600/29; 600/30

(58) Field of Classification Search
USPC ............... 607/39, 40, 41, 118, 138, 133, 143; 600/29–30; 128/DIG. 25
See application file for complete search history.

(56) References Cited

U.S. PATENT DOCUMENTS

| | | | |
|---|---|---|---|
| 6,185,452 | B1 | 2/2001 | Schulman et al. |
| 6,907,293 | B2 | 6/2005 | Grill et al. |
| 7,006,870 | B1 | 2/2006 | Whitehurst et al. |
| 7,054,689 | B1 | 5/2006 | Whitehurst et al. |
| 7,276,057 | B2 | 10/2007 | Gerber |
| 7,328,068 | B2 | 2/2008 | Spinelli et al. |
| 7,328,069 | B2 | 2/2008 | Gerber |
| 7,369,894 | B2 | 5/2008 | Gerber |

(Continued)

FOREIGN PATENT DOCUMENTS

| | | |
|---|---|---|
| WO | WO 2009/018518 | 2/2009 |
| WO | WO 2009/023543 | 2/2009 |
| WO | WO 2009/080784 | 7/2009 |
| WO | WO 2009/080786 | 7/2009 |

OTHER PUBLICATIONS

Boggs, Joseph W. et al., "Bladder emptying by intermittent electrical stimulation of the pudendal nerve," Journal of Neural Engineering, 2006, pp. 43-51 vol. 3.

(Continued)

*Primary Examiner* — Christopher D Koharski
*Assistant Examiner* — Natasha Patel
(74) *Attorney, Agent, or Firm* — Thorpe North & Western LLP (57) ABSTRACT

Methods and related systems for treating patients suffering from several disorders including bladder dysfunction, erectile dysfunction, and bowel elimination disorders are disclosed and described. The method can include identification of the disorder followed by the step of accessing a pudendal nerve of the patient. A microelectrode array having a plurality of electrodes thereon is inserted into the pudendal nerve of the patient. A controller is electronically associated with the microelectrode array which is programmed to provide selective activation and/or blocking of various muscles using the microelectrodes of the array. The selective stimulation can be tuned to selectively activate or block at least one muscle selected from the group consisting of the external urethral sphincter, the detrusor muscle, the anal sphincter, and the cavernous smooth musculature of the penis.

14 Claims, 6 Drawing Sheets

(56) References Cited

U.S. PATENT DOCUMENTS

| | | |
|---|---|---|
| 7,427,280 B2 | 9/2008 | Gerber |
| 7,437,194 B2 | 10/2008 | Skwarek et al. |
| 7,565,198 B2 | 7/2009 | Bennett et al. |
| 7,571,000 B2 | 8/2009 | Boggs, II et al. |
| 7,580,752 B2 | 8/2009 | Gerber et al. |
| 2002/0055761 A1* | 5/2002 | Mann et al. .............. 607/41 |
| 2004/0049240 A1 | 3/2004 | Gerber et al. |
| 2005/0021108 A1* | 1/2005 | Klosterman et al. ........ 607/48 |
| 2005/0113877 A1 | 5/2005 | Spinelli et al. |
| 2005/0113878 A1 | 5/2005 | Gerber |
| 2006/0184211 A1* | 8/2006 | Gaunt et al. .............. 607/48 |
| 2007/0112404 A1 | 5/2007 | Mann et al. |
| 2007/0260288 A1* | 11/2007 | Gross .............. 607/41 |

OTHER PUBLICATIONS

Pikov, Victor et al., "Intraspinal stimulation for bladder voiding in cats before and after chronic spinal cord injury," Journal of Neural Engineering, 2007, pgp. 356-368, vol. 4.

* cited by examiner

SYSTEMS AND METHODS FOR TREATING DISORDERS BY SELECTIVELY ACTIVATING AND/OR BLOCKING MUSCLES THROUGH INTRAFASICULAR STIMULATION OF THE PUDENDAL NERVE

RELATED APPLICATION

This application claims the benefit of U.S. Provisional Patent Application 61/102,255, which was filed Oct. 2, 2008, and which is incorporated herein by reference.

FIELD OF THE INVENTION

This invention relates to systems and methods relating to the treatment of physiological disorders through the artificial direct stimulation of the pudendal nerve.

BACKGROUND

Bladder dysfunction affects 17 million Americans. Current treatments include long-term catheterization, major reconstructive surgery, or functional electrical stimulation of the sacral roots. Catheterization is commonly used but it is accompanied by many side effects, including: insertion difficulty, repeated urinary tract infections, urethral damage and inflammation, and social incompatibility. For many patients with spinal cord injury or neurological disease, indwelling or intermittent catheterization is ineffective or unmanageable. Bladder reconstructive procedures are extensive, only modestly successful, still require intermittent catheterization or wearing of an external urinary stoma bag, and may have substantial associated complications. Functional electrical stimulation at various parts of the urogenital system has been of some success. Functional electrical stimulation of the anterior roots of S2, S3 and S4 has emerged as a fairly successful method for emptying the bladder in some patients with spinal cord injury. This approach is based upon 'post stimulus voiding' where both detrusor and EUS are periodically briefly stimulated and brief voids are evoked at the end of each stimulus. Functional electrical stimulation eliminates many of the side effects of catheterization including urinary tract infections and urethral damage. However, while sacral root stimulation activates detrusor contraction, this in turn causes reflexive activation of EUS. In order to prevent contraction of the EUS upon electrical stimulation (which would block urinary flow) it is necessary to transect the dorsal root sensory neurons (a dorsal rhizotomy), which may lead to a loss of any residual sensation, reflex erection and ejaculation in the male, or vaginal lubrication in the female. Similar challenges are faced in the treatment of erectile dysfunction and bowel elimination disorders. In light of this, research continues in an effort to create major improvements in clinical treatments of these disorders.

SUMMARY

A method of treating patients suffering from several disorders including bladder dysfunction, erectile dysfunction, and bowel elimination disorders is provided. After identification of the disorder, a pudendal nerve of the patient is accessed. A microelectrode array having a plurality of electrodes thereon is inserted into the pudendal nerve of the patient. A controller is electronically associated with the microelectrode array which is programmed to provide selective activation or blocking of various muscles using the microelectrodes of the array. The selective stimulation can be tuned to selectively activate at least one muscle selected from the group consisting of the external urethral sphincter, the detrusor muscle, the anal sphincter, and the cavernous smooth musculature of the penis.

In a related embodiment, a system for the treatment of bladder dysfunction, erectile dysfunction, and bowel elimination disorders is provided. The system can include a first microelectrode array having a plurality of microelectrodes. The first microelectrode array can be configured for implanting into a pudendal nerve of a patient. The system further includes a controller that is electronically associated with the first microelectrode array and that can be programmed to provide simultaneous low frequency stimulation by one or more microelectrodes to activate a first muscle and high frequency stimulation by one or more other microelectrodes to block a second muscle. Optionally, additional muscle groups can be activated or blocked using yet other microelectrodes of the array. The first and second muscles are independent from each other and can be selected from the group consisting of the detrusor muscle, the anal sphincter, and the cavernous smooth musculature of the penis.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

DETAILED DESCRIPTION OF EXEMPLARY EMBODIMENTS

The following detailed description of exemplary embodiments of the invention makes reference to the accompanying drawings, which form a part hereof and in which are shown, by way of illustration, exemplary embodiments in which the invention may be practiced. While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

The following detailed description and exemplary embodiments of the invention will be best understood by reference to the accompanying drawings, wherein the elements and features of the invention are designated by numerals throughout.

DEFINITIONS

In describing and claiming the present invention, the following terminology will be used.

The singular forms "a," "an," and "the" include plural referents unless the context clearly dictates otherwise. Thus, for example, reference to "an array" includes reference to one or more of such materials and reference to "subjecting" refers to one or more such steps.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, the term "bladder dysfunction" refers to any condition in which a patient has difficulty in or cannot control bladder function. Non-limiting examples of conditions which qualify as bladder dysfunction include urinary incontinence, limited voiding, and the like.

As used herein, the term "erectile dysfunction" refers to any condition which prevents male sexual function including stimulation, ejaculation and the like.

As used herein, the term "bowel elimination disorders" refers to any condition in which a patient has problems with controlling defecation. Non-limiting examples of conditions would qualify as bowel elimination disorders include fecal incontinence, inability to defecate and the like.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

In the present disclosure, the term "preferably" or "preferred" is non-exclusive where it is intended to mean "preferably, but not limited to." Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

One embodiment can include a method of treating patients suffering from several disorders including bladder dysfunction, erectile dysfunction, and bowel elimination disorders. After identification of the disorder, a pudendal nerve of the patient is accessed. A microelectrode array having a plurality of electrodes thereon is inserted into the pudendal nerve of the patient. A controller is electronically associated with the microelectrode array which is programmed to provide selective stimulation to various muscles using the microelectrodes of the array. The selective stimulation can be tuned to selectively activate or block at least one muscle selected from the group consisting of the external urethral sphincter, the detrusor muscle, the anal sphincter, and the cavernous smooth musculature of the penis.

In another embodiment, a system for the treatment of bladder dysfunction, erectile dysfunction, and bowel elimination disorders is provided. The system can include a first microelectrode array having a plurality of microelectrodes. The first microelectrode can be configured for implanting into a pudendal nerve of a patient. The system further includes a controller that is electronically associated with the first microelectrode array and that can be programmed to provide simultaneous low frequency stimulation by one or more microelectrodes to stimulate a first muscle and high frequency stimulation by one or more other microelectrodes to stimulate a second muscle. Typically, stimulation of the first muscle can provide activation or contraction while high frequency stimulation of the second muscle provides blocking or relaxation. Alternatively, additional muscles can be activated or blocked by stimulating yet other microelectrodes of the array. The first and second muscles are independent from each other and can be selected from the group consisting of the detrusor muscle, the anal sphincter, and the cavernous smooth musculature of the penis.

Figure 1A:
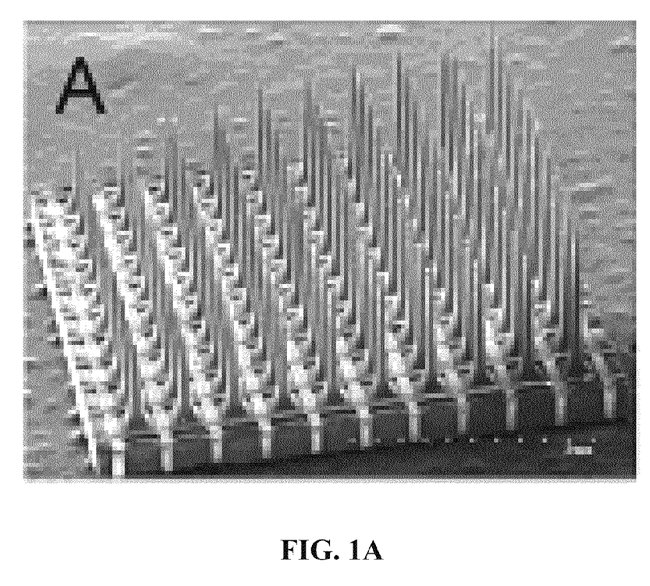
FIG. 1A is an image of a Utah Slant Electrode Array (USEA).
Figure 1B:
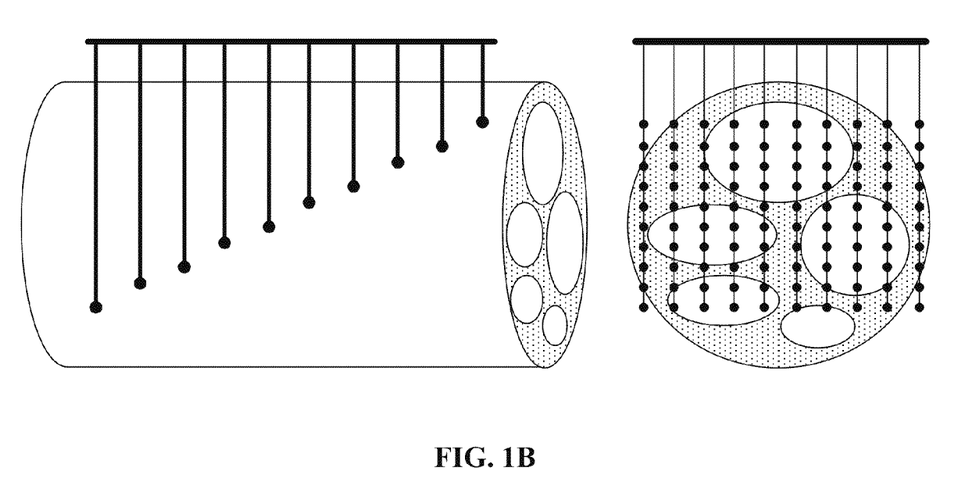
FIG. 1B is a cross sectional and longitudinal depiction of a USEA implanted into a nerve.

The microelectrodes used in the systems and methods of the present invention can be implanted anywhere along the pudendal nerve using any surgical technique known in the art. Once implanted, the electrodes of the microelectrode arrays penetrate into the pudendal nerve. The microelectrode arrays that can be used include those known as "Utah Electrode Arrays" (UEA) including flat Utah Electrode Arrays described in U.S. Pat. No. 5,215,088, which is incorporated by reference; the contoured Utah Electrode Arrays (contoured UEA) disclosed in U.S. patent application Ser. No. 11/807,766 (U.S. Application Publication No. 2008/0138583) which is incorporated by reference; planar arrays (i.e. individual microneedles are etched from a single silicon wafer and subsequently assembled into an array); as well as the Utah Slanted Electrode Array (USEA) shown in FIGS. 1A and 1B. In one embodiment, the microelectrode array can include a plurality of microelectrodes that are each electrically individually addressable.

One advantage of the microelectrode arrays used in the systems and methods of the present invention, in particular the Utah Slanted Electrode Array, is that they are capable of penetrating into the pudendal nerve onto which they are attached, thereby disposing the microelectrodes across the pudendal nerve bundle enhancing the ability of the microelectrode array to selectively stimulate the various muscles innervated by the pudendal nerve. In one embodiment, such as when a Utah Slanted Electrode Array is used, each nerve fiber within the pudendal nerve is within 200 microns of at least one microelectrode on the microelectrode array. The ability to place a microelectrode within such close proximity to each nerve bundle allows a single microelectrode array to selectively and independently stimulate multiple muscles and further allows simultaneous stimulation. Such simultaneous stimulation is discussed in further detail below.

The microelectrode arrays can be configured to be electronically associated with a controller that selectively activates the microelectrodes in the microelectrode array. Generally any type of electronic association between the controller and the microelectrode array can be used so long as the controller is able to selectively stimulate the microelectrode array. The microelectrode arrays can be electronically associated with the controller using wires or by using a wireless signaling device. Wireless signaling devices can include radio wave, Wi-Fi, magnetic switching, or other wireless signaling means. When a wireless signaling device is used, a battery can be implanted with the microelectrode array to act as the source of electricity for the microelectrode array stimulation. In one aspect of the invention, the controller can be external to the patient and can be controlled manually by the patient or other individuals. In another embodiment, the controller can be programmed to automatically activate at selected times or time intervals.

The controller that is electronically associated with the microelectrode array can be programmed to provide activation of selected microelectrodes in the microelectrode array, thereby providing selective stimulation of a desired muscle. The controller can be any unit which generates and/or relays electrical signals as described herein. Non-limiting examples of muscles that can be selectively stimulated include the external urethral sphincter, the detrusor muscle, the anal sphincter, and the cavernous smooth musculature of the penis.

The selective stimulation of the muscles in the present invention can be accomplished using different electrical patterns and frequencies. In one embodiment, the selective stimulation can be accomplished using high frequency current. In one aspect of the invention the high frequency current is high frequency alternating current. The high frequency current can have a frequency of from about 0.5 kHz to about 20 kHz. This frequency may be used to block tonically activated muscle(s), thereby relaxing the muscle(s). In another embodiment, the high frequency current can have a frequency of about 1 kHz to about 8 kHz. In yet a further embodiment, the high frequency current can have a frequency of about 1 kHz to about 3 kHz. In one aspect of the invention, the high frequency current can be high frequency alternating current, the frequency can be from about 1 kHz to about 3 kHz and the muscle being selectively stimulated can be the external urethral sphincter. It has been discovered that high frequency stimulation of the nerve fibers innervating the external urethral sphincter (EUS) can effectively block the signals along the efferent nerve fibers controlling the external urethral sphincter, thereby allowing the EUS to relax. The relaxation of this muscle greatly enhances the effectiveness of the voiding of the bladder.

In another embodiment, the selective stimulation can be accomplished by low frequency stimulation. For the purposes of the present invention, low frequency is from about 5 Hz to about 100 Hz. In another embodiment, low frequency can be from about 10 Hz to about 50 Hz. In yet a further embodiment, the selective stimulation can be accomplished with a low frequency current having a frequency of about 10 Hz to about 50 Hz and the muscle being selectively stimulated can be the detrusor muscle of the bladder.

The controller can be programmed to provide selective stimulation on a single frequency or on multiple frequencies on single or multiple electrodes. For example the controller can be programmed so that one electrode of the micro electrode array provides selective stimulation using a low frequency while a second electrode in the micro electrode array provides selective stimulation using high frequency stimulation. The ability of the methods and systems of the present invention to simultaneously provide selective stimulation at different frequencies can greatly enhance the effectiveness of the treatment of the targeted disorder. For example, in order to void the bladder the detrusor muscle must contract while the external urethral sphincter simultaneously relaxes. Contraction of one muscle simultaneously with the relaxation of another muscle is difficult to achieve through single frequency stimulation. In fact, in many cases single frequency stimulation provides poor results for treating conditions that involve the simultaneous contraction of one muscle and the relaxation of another muscle.

In one aspect of the invention the controller can be programmed to provide low frequency stimulation that stimulates tonic activation of the detrusor muscle while simultaneously using high frequency stimulation to stimulate efferent nerve fibers that innervate the external urethral sphincter causing the external urethral sphincter to relax.

In some situations it may be desirable to utilize a second microelectrode array in conjunction with the first microelectrode array in order to greater enhance the ability of the system or method to treat the targeted disorder. In one embodiment, a second microelectrode array can be implanted on the first or same pudendal nerve as the first microelectrode array and electronically associated to the controller. In another embodiment, a second microelectrode array may be implanted on a second pudendal nerve and electronically associated with the controller. Thus, there are two pudendal nerves on each side of the body. Therefore, implanting one or more arrays only on one side would provide unilateral stimulation and implanting one or more arrays on each side provides bilateral stimulation. The choice of number and placement of arrays along these pudendal nerves can be varied for a particular patient, desired function and/or optimization to achieve target functionality. For example, in some cases a unilateral approach may be sufficient while in other cases a bilateral approach would be needed to achieve desired results.

EXAMPLES

Example 1

Tests were performed using large dogs weighing ~20 kg. The dogs were anesthetized with an IM injection of telezol (9-12 mg/kg) and surgery was performed under mechanical ventilation with inhalation anesthesia provided with isoflurane (1.5-2%). Access to the pudendal nerve was gained through the dissection of the ischioanal fossa. An incision was made between the base of the tail and the ichial tuberosity. Blunt dissection of the ischioanal fossa exposes the pudendal nerve, which lies lateral to the coccygeus muscle and deep to the superficial gluteal muscle. Here the pudendal nerve divides into the sensory and rectal perineal branches. The USEA was inserted into the nerve proximal to any observable branching point using our pneumatic high velocity inserter technique. After implantation, a Pt/Ir return wire electrode (201R2T, Medwire) was placed in nearby muscle or fascia. After exposure of the pudendal nerve, two catheters were inserted through the bladder wall for monitoring bladder pressure and for the filling of the bladder with saline; fine wire electrodes were inserted into the EUS for monitoring EUS electromyographic potentials (EMGs); a catheter was inserted in the urethra; and a USEA was implanted into the pudendal nerve. Following surgical procedures, gas anesthesia was stopped and alpha chloralose anesthetic was administered IV (65 mg/kg) and periodically supplemented (15 mg/kg every 1.5 hrs) throughout the remainder of the experiments. Alpha chloralose was used as it does not inhibit spinal cord reflexes making it a more appropriate anesthetic for physiological studies of the mechanisms of micturition. Animals were monitored for core temperature, oxygen saturation and heart rate with pulse oxymetry, and exhaled CO2 using capnography. Animal temperature was maintained with a heated water blanket. The animal was positioned in a prone posture with most of the animal's trunk weight supported with rolled towels.

Data Acquisition and Stimulation Parameters

Data was collected and stored using the Cerebus data acquisition system (Blackrock Microsystems Inc., Salt Lake City, Utah). An integrated platform developed in the Normann Laboratory was used for stimulation and recording parameters. Analog data from our stimulator, bladder pressure transducer (Deltran DPT-100, Utah Medical Products, Salt Lake City, Utah), and EMG fine wire electrodes were sampled at 10 kSamples/sec and stored to binary files on a hard disk through the standard Windows file I/O interface. Voiding was monitored by urine collection using a recording balance (Setra EL200S, Boxborough, Mass.) and data was stored on a separate PC. Data analysis was done using Matlab (Mathworks Software, Natick, Mass.). Stimulation was generally monophasic and cathodic with constant voltage. Pulse width modulated constant voltage monophasic stimuli and constant current stimulation were both used.

Distention-Evoked Detrusor Contractions

Figure 2:
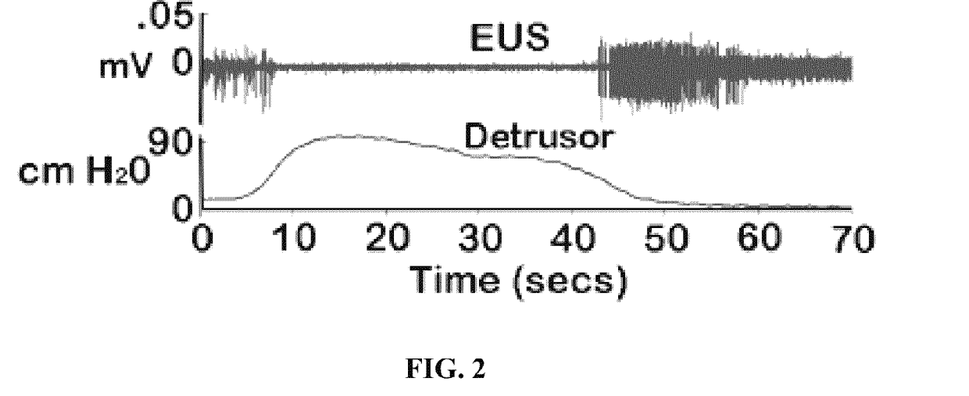
FIG. 2 graphically shows the detrusor pressure increases over time associated with a distension evoked contraction. The bottom trace shows detrusor pressure increase and the top trace shows external urethral sphincter (EUS) electromyographic (EMG) activity.

To ensure that all instrumentation was working correctly and that the surgical procedures and alpha chloralose anesthetic did not produce any pathological complications, a series of bladder filling experiments were performed in order to produce distention-evoked contractions. FIG. 2 shows the distension evoked contractions and the detrusor pressure increases over time. Spontaneous contractions of up to 60-80 cm $H_2O$ were occasionally evoked, with durations as long as 30-40 sec, with bladder pressures more frequently measuring about 40 cm $H_2O$ and having durations of 10-15 seconds. It is noteworthy that these values are comparable to those observed in humans. Distention-evoked contractions were typically accompanied by elimination of EUS EMGs that were followed by a reflexive reconstriction of the urethral sphincter, see the top trace of FIG. 2. This indicates that the circuitry underlying reflex continence is intact and that the EMG electrodes were correctly implanted into the external urethral sphincter. In many cases the contractions were associated with varying degrees of voiding. The contraction shown in FIG. 2 produced a 66 mL void. The presence of distention-evoked contractions shows that alpha chloralose anesthesia does not abolish spinal cord reflexes as would other anesthetics such as isoflurane.

Mapping of USEA Electrodes to the Detrusor and EUS

The diameter of the pudendal nerves of the 8 dogs studied ranged from 2-3 mm in diameter. The back plane of a USEA that is implanted into the pudendal nerves of the dogs is 4 mm×4 mm so many electrodes on each side of the array were outside of the implanted nerves. Accordingly, a map of electrodes that evoked physiological responses was produced. This was done by stimulating each of the 100 electrodes sequentially and observing any evoked changes in bladder pressure and/or sphincter EMGs. Typically, from 4-10 electrodes produced a sustained EUS EMG, and a separate 2-5 electrodes produced a transient increase in bladder pressure.

Activation of Detrusor with Low Frequency Stimulation

Figure 3:
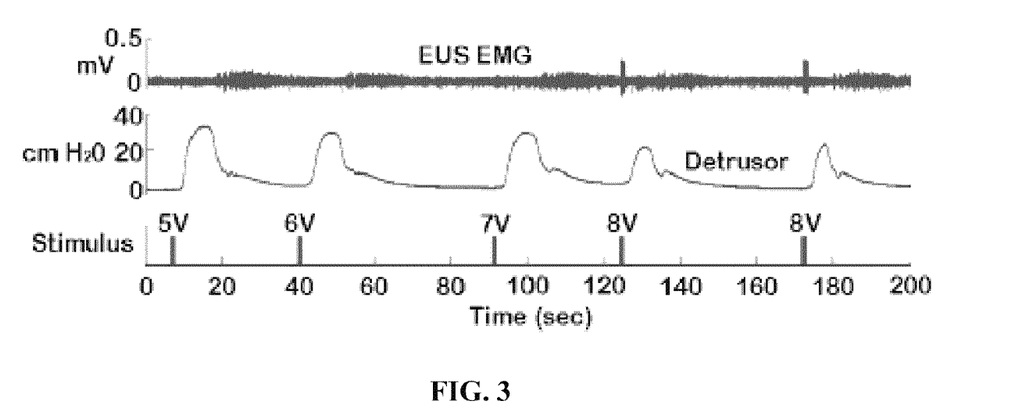
FIG. 3 graphically shows the selective activation of detrusor bladder muscle using a USEA. Bladder pressure is increased by the five periods of stimulation.
Figure 4:
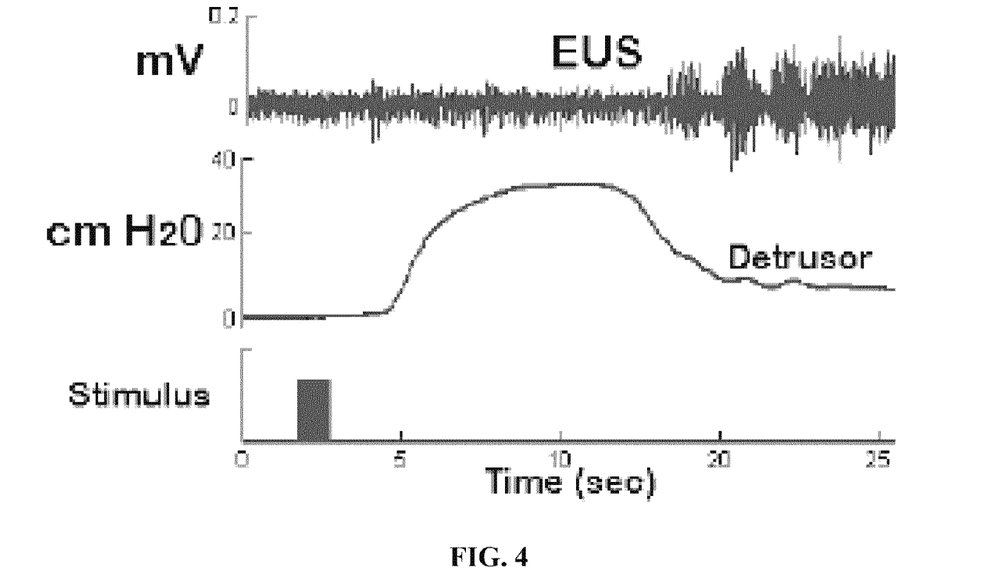
FIG. 4 graphically shows the faster sweep spread of detrusor activation after stimulating electrode 92 of a USEA at 5 V.

Our preliminary efforts to evoke contractions of the detrusor with extrinsic stimulation via the implanted USEA also produced variable results. In our early experiments (while improvements in instrumentation and surgical techniques were being made), Detrusor contractions were initiated and were manifested as transient increases in bladder pressure. FIG. 3 shows a record of five successive detrusor contractions that were evoked by five sequential electrical stimulations delivered via one of the electrodes in the USEA that was implanted in the pudendal nerve (electrode 92, 2V threshold, 33 Hz, 1 sec, 200 μsec monophasic stimuli). The smaller increases in bladder pressure evoked by the last two periods of stimulation suggest that rate of stimulation produced fatigue in the detrusor or activated competing pathways. Note that when the stimulation voltage reached 8 volts, the injected currents appeared to have spread in the pudendal nerve to the point that the EUS efferents were stimulated. This can be seen as the bursts in the EUS EMG as shown in the top trace of FIG. 3. Each period of detrusor activation was followed by a period of increased EUS activation. In this set of experiments, the kinetics of the stimulus evoked contractions that were of similar amplitudes and kinetics to the distention-evoked contractions. FIG. 4 shows one of the stimulus evoked detrusor contractions on a faster time scale. These contractions were achieved using selective activation of the detrusor with 5 of the 100 USEA electrodes. The kinetics of these stimulus evoked bladder pressure increases suggest that pudendal nerve stimulation is acting via the reflexive pathway.

Sustained detrusor contractions were produced using prolonged low frequency (33 Hz, 60 sec, 200 usec, monophasic) stimulation via single electrodes from a USEA implanted in the pudendal nerve. One minute of stimulation produced a prolonged increase in bladder pressure (and pressures recorded at the EUS and the bladder neck), and an increase in EMG recorded at the EUS. Without being limited by theory, it is possible that this EUS EMG may have resulted from a small amount of EUS excitation due to the stimulation not being fully selective to the detrusor, from afferent feedback to the EUS, from detrusor excitation, and/or from stimulation artifact. This increase in bladder pressure also produced a small degree of voiding which may have been due to leakage around the catheter. It is worth noting that upon termination of the detrusor activation, a small, transient increase in voiding was recorded, possibly due to a brief relaxation of the EUS.

Selective Excitation of the EUS

Figure 5:
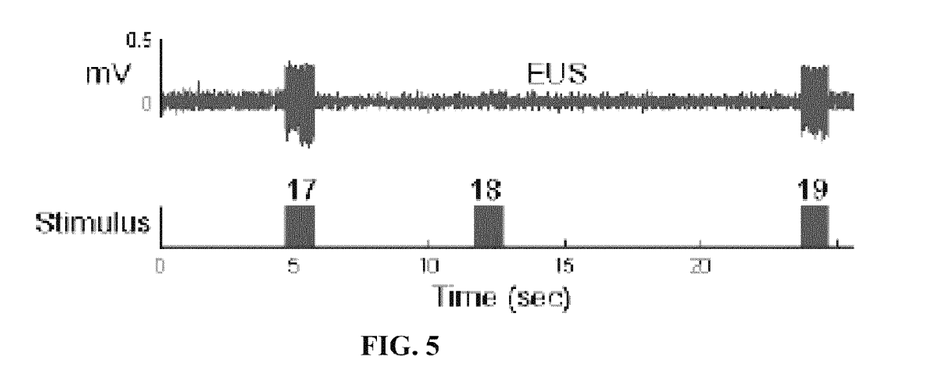
FIG. 5 graphically shows the selective activation of an external urethral sphincter using a USEA. The sphincter was activated by stimulating electrodes 17 and 19. Stimulation of electrode 18 showed no sphincter activation (in other words no EMG from the EUS).

USEAs were implanted in the pudendal nerve so that a number of electrodes were located adjacent to efferent fibers that innervated the EUS. An example of such EUS targeted electrode selectivity is shown in FIG. 5 where one second periods of stimulation (33 Hz, 200 μsec, monophasic, cathodic) via electrodes number 17 and 19 evoked a burst of EMG activity in the EUS. The highly selective stimulation capabilities of the USEA and of this EUS targeting can is demonstrated by the fact that electrode number 18 did not provide any effect even though it was located in between electrodes 17 and 19. These low frequency evoked EUS EMG waveforms were used in the mapping of electrodes described above. Selective bursting of the EUS in 20 of the 100 microelectrodes in the USEA was observed. The location of each electrode was mapped in order to determine if the electrodes that activated either detrusor or EUS were grouped together on the USEA. It was found that electrodes that activated EUS or detrusor were spatially organized into different regions in the nerve.

Relaxation of EUS with High Frequency Stimulation

Once the electrodes that targeted the EUS were identified, high frequency stimulation to block the normal efferent activity that keeps the EUS in its contracted state was applied. As a prelude to these experiments, experiments in the feline sciatic nerve were performed to investigate if intrafascicular high frequency stimulation was effective at blocking efferent activity in nerves innervating the musculature of the hind limb. The results of the experiments are briefly summarized herein.

Two hook electrodes were placed around the sciatic nerve of the feline and evoked forces at the foot were monitored with a force plate. Individual muscle excitation was monitored with fine wire electrodes inserted into the major extensor and flexor muscles of the ankle. The proximal hook was used to produce periodic twitches and the distal hook was used to deliver high frequency current for blocking efferent activity. As has been previously reported by others, the high frequency stimulation (2 kHz, 2 V peak to peak sinusoidal stimulation) produced an initial large transient force followed by a complete elimination of force and EMGs in the instrumented muscles.

Figure 6:
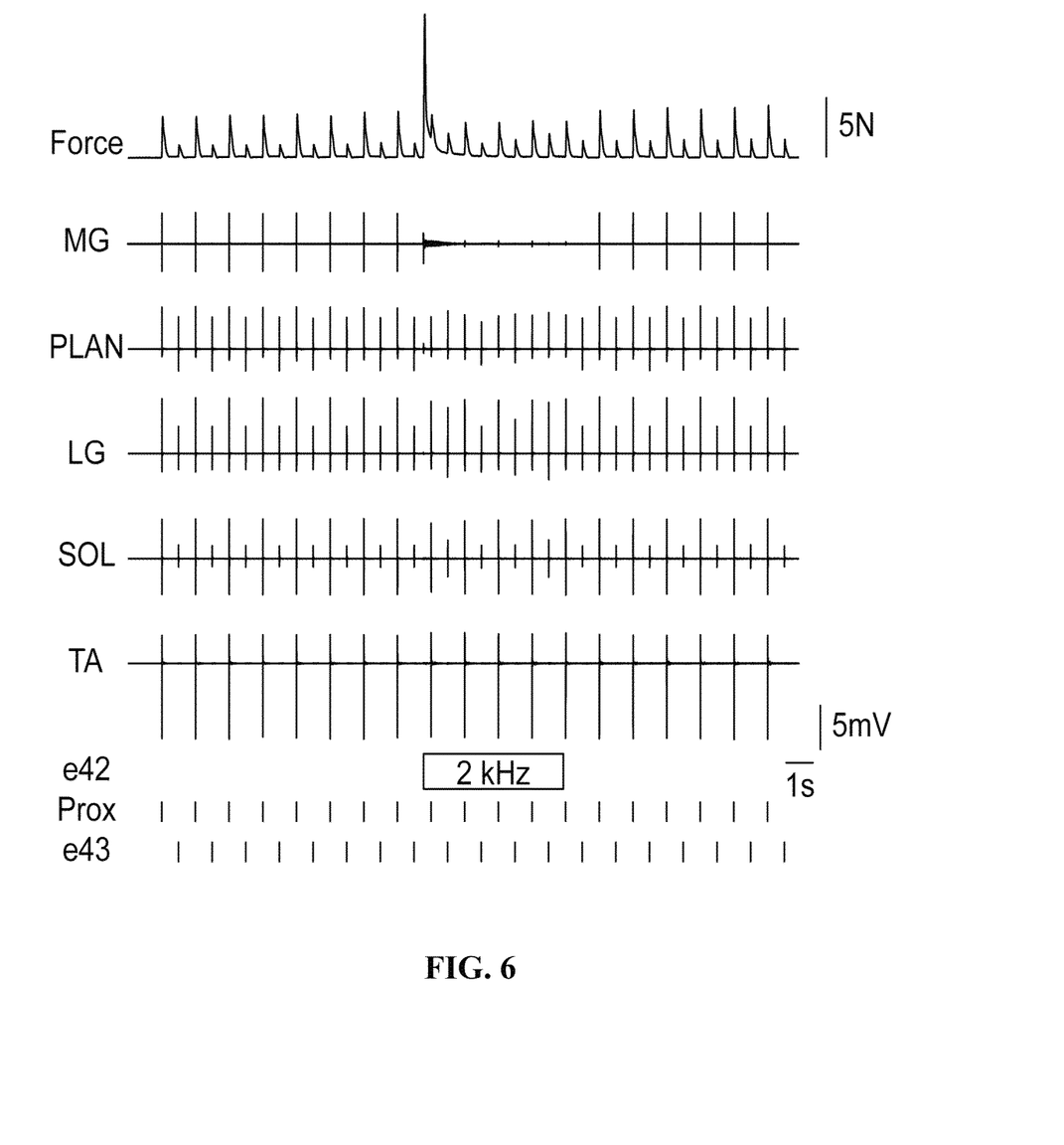
FIG. 6 graphically shows selective block of efferent excitation of medial gastrocnemius muscle by high frequency (2 kHz) stimulation delivered via one electrode in a USEA implanted in a cat sciatic nerve.

It was further investigated whether intrafascicular high frequency stimulation could produce selective blockade of targeted muscles. The results of these experiments are summarized in FIG. 6. As was used for the hook electrode block described above, periodic stimulation was delivered via a proximal hook electrode (Prox). Periodic stimulation (out of phase from the hook stimulation) was also delivered via one of the electrodes (e43) in a USEA that was implanted distal to the hook. The EMGs evoked in the ankle extensor muscles were monitored with fine wire electrodes. A second USEA electrode (e42) was identified that selectively evoked twitches in the medial gastrocnemus muscle, and this electrode was used to deliver the 3.5 V, 2 kHz sinusoidal blocking stimulus. The blocking stimulus was highly selective: it eliminated EMGs in the medial gastrocnemus muscle evoked by the proximal hook electrode, but was without effect on the other extensor muscles of the ankle that were instrumented with fine wire EMG electrodes. The experiment illustrated in FIG. 6 also shows that selective blocking can be produced with intrafascicular stimulation even while selective stimulation is produced with other intrafascicularly implanted electrodes: e43 is able to selectively excite plantaris and lateral gastrocnemeus (and to a lesser degree soleus) without exciting tibialis anterior or medial gastrocnemus, and that this selective excitation continues even when the medial gastrocnemeus block is delivered via e42.

Using a similar experimental paradigm, experiments were also performed in the cat sciatic nerve to demonstrate that selective intrafascicular blocking could be produced for 30 minutes (the longest periods studied). These experiments demonstrated selective intrafascicular blocking in cat sciatic nerve and prompted further investigation into intrafascicular blocking of efferent activity the dog pudendal nerve.

Experiments using high frequency blocking of tonic EUS contraction were performed. Monitoring of the status of EUS activation was attempted using three approaches. Fine wire EMG electrodes were implanted in the muscles of the EUS, we monitored EUS pressure with a dual sensor pressure monitoring catheter (model CTC/4F2, MMI, Hackensack, N.J.) voiding during EUS blocking was measured. Results were somewhat inconsistent. Background level of EMG activity in the EUS as the bladder was being filled with saline was significantly reduced during distention-evoked contractions and transiently increased as bladder pressure returned to its pre-distention value (see FIG. 2). This EMG signature is what might be expected during a voiding maneuver and this signature was seen during some voids. However, in other experiments, EUS EMGs were seen throughout the periods of voiding. Low frequency electrical stimulation of subsets of USEA electrodes implanted in the pudendal nerve often evoked EMG bursts that were sustained as long as stimulation proceeded (see FIG. 5).

Figure 7:
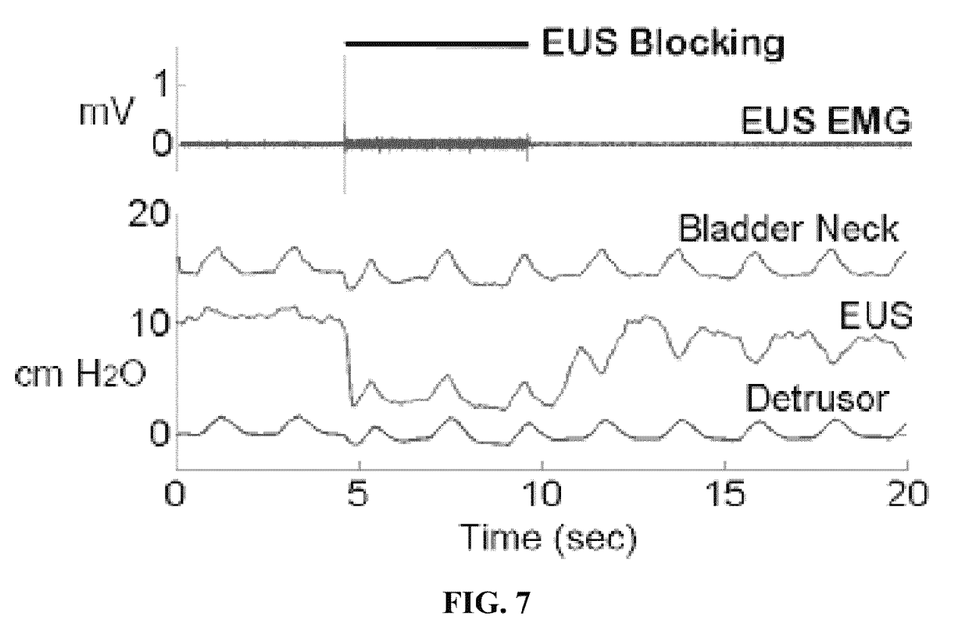
FIG. 7 graphically shows relaxation of the EUS evoked by high frequency stimulation via electrode 51 on a USEA. The traces are from top to bottom: EUS blocking stimulus; EUS EMG and pressures at the bladder neck, EUS, and bladder (detrusor).

Additional testing was done to measure EUS pressure directly with a pressure sensing catheter positioned at the EUS (this was only attempted in one animal). Positioning of the catheter was determined by inserting it into the bladder and then slowly withdrawing it while sensor pressure was continuously monitored. At a position near the EUS, an increase in pressure was measured, and the catheter was slowly moved back and forth until a maximum in pressure was recorded. Pressure recording during gentle palpation of the urethra around the location of the EUS provided additional confidence that the sensor was located in the EUS. The catheter also contained a second pressure sensor located on its tip and this sensor was probably located near the bladder neck. Finally, another independent catheter was inserted through the bladder wall and this was connected to an external Utah Medical pressure sensor. These pressure sensors were intended to monitor bladder pressure, pressures at or near the bladder neck, and the pressure at the EUS and demonstrated that EUS pressure could be selectively decreased. FIG. 7 shows an example of pressure recordings during high frequency (2 kHz) stimulation via an individual USEA electrode implanted in the pudendal nerve. High frequency stimulation had virtually no effect on either bladder neck pressure or bladder pressure, but decreased pressure in the EUS (note that the pressure records in this figure have been displaced vertically so absolute mean pressures cannot be inferred). It is noteworthy that that EUS pressure before stimulation manifests little respiratory artifact, but during high frequency stimulation a respiratory artifact similar in amplitude and phase to pressures at the bladder neck and bladder itself is observed (possibly reflecting pressure variations in the bladder). However, at the end of high frequency stimulation of the EUS, the respiratory artifact inverts in phase. Similar complexities were also seen in other experiments where high frequency stimulation was occasionally seen to produce an apparent increase in pressure in the EUS (contrary to expectation).

Figure 8:
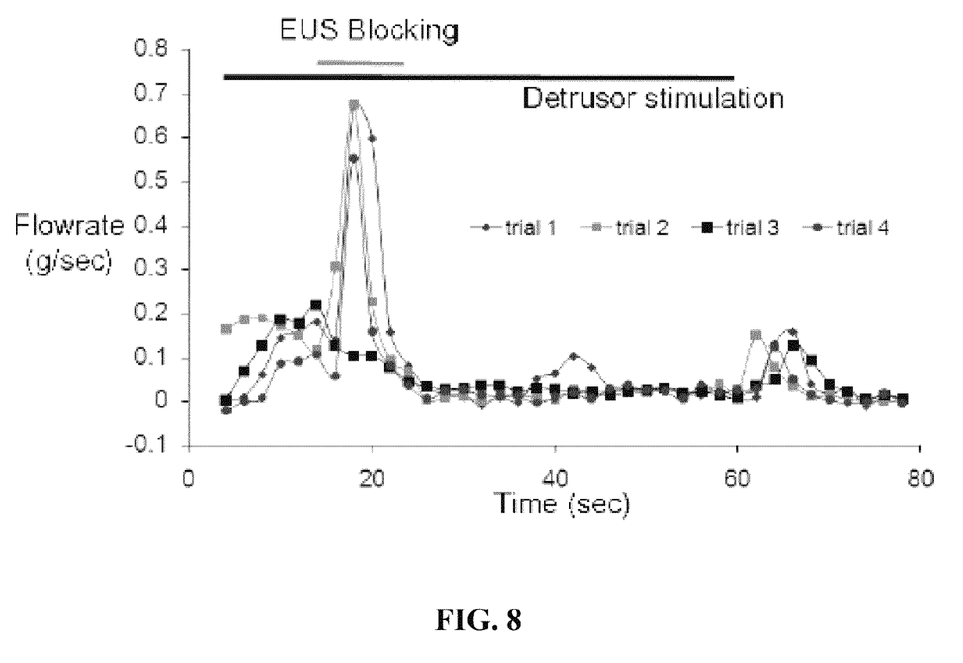
FIG. 8 graphically shows controlled voiding of the bladder by low frequency stimulation of the detrusor and high frequency blocking of the EUS.

Controlled Voiding Produced by Coordinated EUS Relaxation and Detrusor Activation Controlled voiding was accomplished by blocking EUS during a period of prolonged detrusor activation. The results of this experiment are shown in FIG. 8. In this experiment, one minute of 33 Hz stimulation was delivered via an electrode from a USEA implanted in the pudendal nerve that evoked a contraction of the detrusor. Approximately 15 seconds after the onset of detrusor stimulation, 2 kHz blocking stimulation was delivered for ten seconds via a second USEA electrode that targeted EUS. FIG. 8 shows that the blocking stimulus relaxed EUS and produced a controlled void. The experiment was repeated four times. In the first two trials and the last trial, the blocking stimulus was delivered and voiding was produced. In the third trial, no blocking stimulus was delivered, and no voiding was produced.

The detrusor and EUS stimuli were produced by separate stimulators that were manually triggered by the experimenters. As such, the durations of the stimulations, and the sequencing of the two stimulators was somewhat imprecise (accurate to about a second). Also, there was no accurate synchronization between the computer that recorded voided weights and the two stimulators (also accurate to about a second). The evoked voiding was relatively small, but this was apparently due to problems with the urethral catheterization. Further, the duration of the void was transient, and not as long as the EUS blocking stimulus. This appears to indicate that periodic EUS blocking may be required to produce a more compete void. The results shown in FIG. 8 support the concept that intrafascicular high and low frequency stimulation of selected efferent and afferent fibers in the pudendal nerve can produce controlled voiding.

Example 2

Animals were intubated and anesthesia was maintained with α-chloralose (65 mg/kg initial; 15 mg/kg supplemental). A ventral midline incision was made to expose the detrusor bladder muscle and urethral sphincter. One catheter was inserted into the urethra and two into the bladder in order to measure voided volume, pressure, and for bladder filling respectively. Electromyographic (EMG) electrodes were inserted into the external urethral sphincter (EUS). The pudendal nerve was accessed via ischioanal fossa and a USEA was inserted using a pneumatic pulse inserter technique.

Surgical access to the pudendal nerve can be effectively gained by dissection of the ischioanal fossa. Stimulation of the pudendal nerve using USEA allows for selective activation of muscles of micturition.

Unilateral pudendal nerve stimulation using a USEA may be sufficient to achieve controlled micturition. Activation of detrusor and inhibition of EUS using a USEA may be sufficient to empty the bladder via continuous voiding. High frequency (1-40 kHz) block of EUS efferent fibers may also be accomplished. Coordination of EUS block and detrusor activation can be implemented to control micturition.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:
1. A method of treating a disorder comprising,
    a. identifying a patient suffering from at least one disorder selected from the group consisting of bladder dysfunction, erectile dysfunction, and bowel elimination disorders;
    b. accessing a first pudendal nerve of the patient;
    c. providing a first microelectrode array having a plurality of microelectrodes that are electrically individually addressable, and the plurality of microelectrodes are mounted on a common planar substrate substantially perpendicular to one another;
    d. inserting the first microelectrode array into the first pudendal nerve such that the plurality of microelectrodes penetrate intrafascicularly into the pudendal nerve;
    e. electronically associating a controller with the first microelectrode array; and
    f. programming the controller for selective stimulation by microelectrodes of the first micro electrode array, said selective stimulation being tuned for selective stimulation of at least one muscle selected from the group consisting of the external urethral sphincter, the detrusor muscle, the anal sphincter, and the cavernous smooth musculature of the penis.

2. The method of claim 1, wherein the controller is electronically associated with the microelectrode using a wireless signaling device.

3. The method of claim 1, further comprising a second microelectrode array implanted in the first pudendal nerve and electronically associated with the controller for unilateral stimulation.

4. The method of claim 1, further comprising a second microelectrode array implanted in a second pudendal nerve and electronically associated with the controller for bilateral stimulation.

5. The method of claim 1, wherein the selective stimulation is by high frequency alternating current.

6. The method of claim 5, wherein the high frequency current has a frequency of 0.5 kHz to about 20 kHz.

7. The method of claim 5, wherein the muscle is the external urethral sphincter and wherein the frequency is from about 1 kHz to about 3 kHz.

8. The method of claim 1, wherein the selective stimulation is by low frequency stimulation.

9. The method of claim 8, wherein the muscle is the detrusor muscle and the frequency is about 5 Hz to about 100 Hz.

10. The method of claim 8, wherein the low frequency stimulation is from about 10 Hz to about 50 Hz.

11. The method of claim 1, wherein the selective stimulation includes simultaneous low frequency stimulation by at least one microelectrode and high frequency stimulation by at least one other microelectrode of the first microelectrode array.

12. The method of claim 11, wherein the low frequency stimulation causes tonic activation of the detrusor muscle and wherein the high frequency stimulation stimulates and blocks efferent nerve fibers that innervate the external urethral sphincter causing the external urethral sphincter to relax.

13. The method of claim 1, wherein the microelectrode array is a Utah Slanted Electrode Array, a Flat Utah Electrode Array, a contoured Utah Electrode Array, or a planar array.

14. The method of claim 1, wherein the first microelectrode array is inserted such that each nerve fiber within the first pudendal nerve is within 200 microns of a microelectrode of the first microelectrode array.

* * * * *